United States Patent
Brady et al.

(10) Patent No.: US 12,083,273 B1
(45) Date of Patent: Sep. 10, 2024

(54) VACUUM SHIELD ASSEMBLY FOR ATTACHMENT TO MEDICAL MASKS

(71) Applicant: SafER Medical Products, LLC, Branson, MO (US)

(72) Inventors: Rob Brady, Sarasota, FL (US); Matt Vergin, St. Petersburg, FL (US); Barry Jennings, Largo, FL (US); Mike Winterhalter, Nokomis, FL (US); Richard Blubaugh, Branson West, MO (US); Craig Randall, Branson, MO (US); Misty Denevan, Branson, MO (US); Todd Baker, Walnut Shade, MO (US)

(73) Assignee: Safer Medical Products, LLC, Branson, MO (US)

( * ) Notice: Subject to any disclaimer, the term of this patent is extended or adjusted under 35 U.S.C. 154(b) by 753 days.

(21) Appl. No.: 17/173,724

(22) Filed: Feb. 11, 2021

Related U.S. Application Data

(60) Provisional application No. 63/075,890, filed on Sep. 9, 2020.

(51) Int. Cl.
*A61M 16/00* (2006.01)
*A61M 16/06* (2006.01)
(Continued)

(52) U.S. Cl.
CPC .......... *A61M 16/009* (2013.01); *A61M 16/06* (2013.01); *A61M 16/0816* (2013.01);
(Continued)

(58) Field of Classification Search
CPC ... A61B 90/57; A61M 5/1418; A61M 16/009; A61M 39/10; A61M 39/12;
(Continued)

(56) References Cited

U.S. PATENT DOCUMENTS 3,605,200 A * 9/1971 Vallinotto ................. F16L 3/12
                                                  24/20 TT
4,167,946 A * 9/1979 Sandstrom ........ A61M 16/0493
                                                  D24/112
(Continued)

FOREIGN PATENT DOCUMENTS

CN        103672174 B  *  3/2016   ............ F16L 3/1222
CN        105797246 A      7/2016
(Continued)

OTHER PUBLICATIONS

Exhalo Shield (sovmed.com/wp-content/uploads/2020/07/EXHALO-Introduction-Summary-Soverign-Medical-ed3.pdf; accessed Sep. 26, 2023; available since at least Apr. 3, 2020. (Year: 2020).*
(Continued)

*Primary Examiner* — Samchuan C Yao
*Assistant Examiner* — Nicholas B. Engel
(74) *Attorney, Agent, or Firm* — Allen, Dyer, Doppelt & Gilchrist, P.A.

(57) ABSTRACT

A vacuum shield assembly intended for attachment to an existing medical mask for air suction, nebulization, BIPAP, and/or CPAP. The vacuum shield assembly generally comprises a shield body and a retaining assembly. The retaining assembly may attach the vacuum shield assembly to a vacuum tube of the existing mask, which may be connected to a negative pressure vacuum. The retaining assembly may also be attached to a nebulizer unit or component thereof, or to an oxygen supply tube of a BIPAP or CPAP mask. The shield body may comprise a lower segment, which may comprise a connecting component configured and dimensioned for attachment to, and for a fluid communication, with the retaining assembly. The shield body may be configured and dimensioned to correspond to the geometry of the existing mask. As an example, the shield body may
(Continued)

comprise a substantially concave configuration with a substantially semi-ovoidal edge.

14 Claims, 12 Drawing Sheets

(51) Int. Cl.
*A61M 16/08* (2006.01)
*A61M 16/14* (2006.01)

(52) U.S. Cl.
CPC ........ *A61M 16/0875* (2013.01); *A61M 16/14* (2013.01); *A61M 2202/0208* (2013.01)

(58) Field of Classification Search
CPC ...... A61M 2025/024; A61M 2039/009; A61M 2039/1027; A61M 16/0463; A61M 16/06; A61M 16/0683; A61M 16/08; A61M 16/0816; A61M 16/0875; A01G 17/08; B23P 19/00; B25B 25/005; B25B 13/027; B65D 33/1675; B65D 63/1027; B65D 63/1063; B65D 63/12; B65D 13/16; B65H 75/185; E04B 1/86; E04B 9/008; E04B 9/34; E05B 5/003; E05C 19/022; E05C 3/042; E05C 5/00; F02M 55/004; F02M 55/04; F02M 61/168; F02M 69/465; F16B 2/08; F16L 27/11; F16L 3/04; F16L 3/133; F16L 3/23; F16L 3/233; F16L 3/237; F16L 33/035; F16L 33/22; F16L 37/12; F16L 57/00; F16L 57/06; F21V 21/008; G09F 23/00; G09F 23/0083; G09F 3/20; H02G 3/0481
USPC .......................................................... 128/912
See application file for complete search history.

(56) References Cited

U.S. PATENT DOCUMENTS

| | | | | |
|---|---|---|---|---|
| 4,248,218 A * | 2/1981 | Fischer | ............... | A61M 16/009 128/207.18 |
| 4,683,879 A * | 8/1987 | Williams | .......... | A61M 16/0463 128/207.14 |
| 4,716,615 A * | 1/1988 | Whitehead | ............ | G01F 23/045 15/244.1 |
| 4,770,169 A * | 9/1988 | Schmoegner | ......... | A61M 16/08 128/206.28 |
| 4,794,921 A * | 1/1989 | Lindkvist | .......... | A61M 16/0833 128/203.29 |
| 4,807,617 A * | 2/1989 | Nesti | ...................... | A61M 16/06 128/203.29 |
| 4,919,127 A * | 4/1990 | Pell | .................... | A61M 16/0463 128/207.14 |
| 5,095,564 A * | 3/1992 | Kruger | ................... | F16L 37/008 285/420 |
| 5,311,862 A * | 5/1994 | Blasdell | ................ | A61M 16/06 128/205.24 |
| 5,419,317 A * | 5/1995 | Blasdell | ................ | A61M 16/06 128/205.19 |
| 5,429,683 A * | 7/1995 | Le Mitouard | ..... | A61M 16/0605 128/206.26 |
| 5,592,935 A | 1/1997 | Elstran et al. | | |
| 5,676,133 A | 10/1997 | Hickle | | |
| 5,806,819 A * | 9/1998 | Martone | ................... | F16B 2/22 248/230.1 |
| 6,106,030 A * | 8/2000 | Nader | ................. | F16L 23/0283 277/648 |
| 6,298,525 B1 * | 10/2001 | Margo | ................. | F16L 3/237 24/339 |
| 6,592,558 B2 * | 7/2003 | Quah | ................. | A61M 39/284 128/912 |
| 6,830,049 B2 * | 12/2004 | Augustine | ......... | A61M 16/0409 128/207.14 |
| 7,004,168 B2 * | 2/2006 | Mace | .................... | A61M 16/06 128/206.21 |
| 7,055,784 B2 * | 6/2006 | Stigler | ................ | B60R 16/0215 248/68.1 |
| 7,513,252 B2 * | 4/2009 | Berg | .................... | A61M 16/009 128/205.12 |
| 8,291,905 B2 * | 10/2012 | Moenning, Jr. | ........ | A61M 16/06 128/203.29 |
| 8,479,625 B2 * | 7/2013 | Klepper | ............ | A61M 16/0486 83/13 |
| 8,479,737 B2 * | 7/2013 | Moenning, Jr. | ........ | A61M 16/06 128/203.29 |
| 8,539,953 B2 * | 9/2013 | Moenning, Jr. | ..... | A61M 16/104 128/203.29 |
| 8,631,795 B1 * | 1/2014 | McMurray | ........ | A61M 16/0409 128/207.14 |
| 8,826,905 B2 * | 9/2014 | Nashed | ............. | A61M 16/0891 128/205.13 |
| 8,863,746 B2 * | 10/2014 | Totz | ...................... | A61M 16/04 128/207.14 |
| 9,757,528 B2 | 9/2017 | Rubin | | |
| 9,782,555 B2 * | 10/2017 | Burk | ...................... | A61M 16/06 |
| 9,949,629 B2 * | 4/2018 | Gardner | ............ | A61B 1/00154 |
| 10,188,814 B2 * | 1/2019 | Moenning, Jr. | ... | A61M 16/0816 |
| 10,576,228 B2 * | 3/2020 | Blasdell | ............. | A61M 16/0611 |
| 11,052,208 B2 | 7/2021 | Curran et al. | | |
| 2002/0045796 A1 | 4/2002 | O'Connor et al. | | |
| 2003/0116167 A1 * | 6/2003 | Hooser | .............. | F16M 11/2021 128/912 |
| 2005/0077726 A1 * | 4/2005 | White | ............... | A61M 16/1095 285/272 |
| 2007/0017527 A1 * | 1/2007 | Totz | .................. | A61M 16/0486 128/207.15 |
| 2009/0020128 A1 | 1/2009 | Metzger et al. | | |
| 2009/0229615 A1 * | 9/2009 | Stenzler | ............ | A61M 16/0463 128/207.14 |
| 2010/0122704 A1 * | 5/2010 | Moenning, Jr. | ....... | A61M 16/06 128/206.28 |
| 2010/0180737 A1 * | 7/2010 | Klepper | ............ | A61M 16/0463 83/39 |
| 2011/0163533 A1 * | 7/2011 | Snyder | ................... | F16L 33/035 285/88 |
| 2015/0202473 A1 | 7/2015 | Curran et al. | | |
| 2015/0209535 A1 * | 7/2015 | Cole | ................. | A61M 16/0475 128/202.16 |
| 2016/0074268 A1 | 3/2016 | Breegi et al. | | |
| 2019/0070378 A1 * | 3/2019 | Kanowitz | ......... | A61M 16/0463 |
| 2019/0293096 A1 * | 9/2019 | Ormonde | .................. | F16B 2/10 |
| 2020/0038617 A1 | 2/2020 | Varga et al. | | |
| 2020/0254221 A1 * | 8/2020 | Burkin | .................. | A61M 27/00 |
| 2021/0307872 A1 | 10/2021 | Vizulis et al. | | |
| 2021/0346624 A1 * | 11/2021 | Fiorenza | ............. | A61M 16/009 |

FOREIGN PATENT DOCUMENTS

CN 206007759 U 3/2017
WO WO2021207292 10/2021

OTHER PUBLICATIONS

Machine language translation of Chinese Patent CN-103672174-B; copied from the European Patent Office website; available at: https://worldwide.espacenet.com/patent/search/family/050310565/publication/CN103672174B?q=pn%3DCN103672174B (Year: 2016).*
International Search Report and Written Opinion for PCT/US2021/048141; Nov. 17, 2021; ISA-United States Patent and Trademark Office; entire document.
International Search Report and Written Opinion for PCT/US2021/049619; Feb. 28, 2022; ISA-United States Patent and Trademark Office; entire document.
Sovereign Medical, Inc.; Exhlo Shield; Product Information Sheet; Online; Apr. 3, 2020; entire document; https://sovmed.com/wp-content/uploads/2020/07/EXHALO-Introduction-Summary-Soverign-Medical-ed3.pdf.

(56) References Cited

OTHER PUBLICATIONS

International Search Report and Written Opinion for PCT/US2021/048141; United States Patent Office; Nov. 17, 2021; entire document.

* cited by examiner

VACUUM SHIELD ASSEMBLY FOR ATTACHMENT TO MEDICAL MASKS

FIELD OF INVENTION

The present invention relates to attachments to masks for medical procedures.

BACKGROUND

Medical masks may be used for or for nebulizing a patient or used for Non-Invasive Positive Pressure Ventilation (NIPPV), Bi-level Positive Airway Pressure (BIPAP), Bag-Valve-Mask Resuscitator (BVM), Demand-Valve Resuscitator (DVR), or Constant Positive Airway Pressure (CPAP). Of the masks that currently exist, none are believed to provide a truly efficient means for vacuuming air to create negative pressure, or for implementing a nebulizing or positive pressure procedure and at the same time using negative pressure to vacuum exhaled air from the patient. Accordingly, the industry would benefit by providing a vacuum shield assembly for attachment to a medical mask that may be used for vacuuming exhaled air from patient during nebulization, BIPAP or CPAP. Such a vacuum shield assembly would provide the added benefit of at least partially reducing contact to the mask and/or face of the patient, which may help to counter the risk of contagion of airborne illnesses, e.g., influenza, covid-19, etc., providing added protection to medical providers and staff involved in these procedures and in at least partially reducing the development of fomites from exhaled or aerosolized particles or droplets. Additionally, a benefit in the industry would be provided if such a vacuum shield assembly would be disposable as it would further reduce such risk of contagion. An even further benefit would be provided if such a vacuum shield assembly would be sufficiently versatile to be used as a primary and/or a secondary air vacuuming component, and/or a nebulizing component. Yet a further benefit would be realized if this vacuum shield assembly would be provided in different shapes and sizes to correspond to the geometry and size of the underlying face mask.

SUMMARY

The present invention is directed to a vacuum shield assembly intended for attachment to an existing mask. As used herein, an "existing mask" refers to a suction mask, a mask configured for attachment to a nebulizer, BIPAP, CPAP, BVM, DVR or another related mask, that is already disposed on the head and/or face of a patient. Accordingly, the vacuum shield assembly of the present invention may serve as a primary and/or a secondary suction or vacuum mechanism, which in some embodiments may be connected to a negative pressure vacuum. The vacuum shield assembly generally comprises a shield body and a retaining assembly. The retaining assembly may be used to connect the vacuum shield to a vacuum tube connected to a negative pressure vacuum. The retaining assembly may also be attached to a nebulizer unit or component thereof, or to the oxygen supply tube of a BIPAP or CPAP mask. Additionally, the shield body may comprise a lower segment. The shield body may be configured with or without a circular access opening in the convexity of the shield body that will allow a BVM, or DVR to connect to an existing mask by way of the access opening in order to facilitate the vacuuming of exhaled air during said procedures. The lower segment may further define an interior or inside of the shield body and may comprise a connecting portion disposed in fluid communication with the retaining assembly and the vacuum tube. The shield body may be configured and dimensioned to correspond to the geometry of the existing mask. As an example, the shield body may comprise a substantially concave configuration and/or a variety of shapes, including, but not limited to, a substantially triangular or substantially ovoidal shape. However, other shapes of the shield body are possible, which may also to correspond to the shape of the existing mask and/or the shape of the face and/or head of the patient. As such, it is within the scope of the present invention that the vacuum shield assembly according to the present invention at least partially remove exhaled infectious particles, for example, from a patient that has a respiratory illness. As a result, it is contemplated that such increased removal of exhaled infectious particles at least partially reduce the risk of contagion of medical practitioners and staff assisting with these types of procedures and/or the contamination of physical objects in the vicinity (fomites).

DETAILED DESCRIPTION

Figure 1:
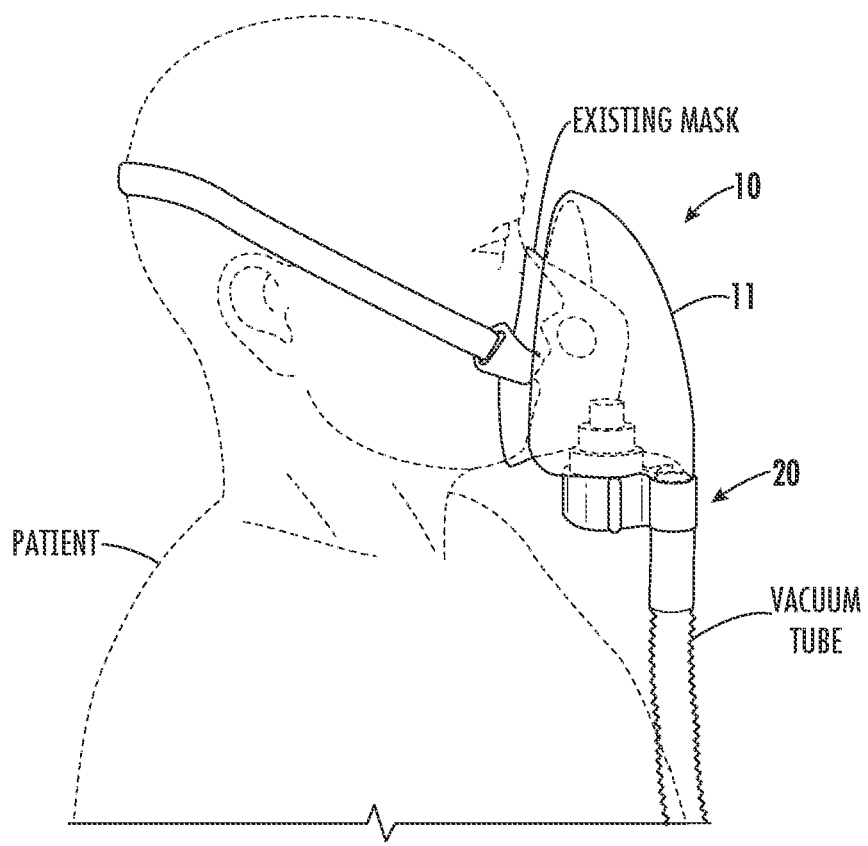
FIG. 1 is a perspective view of one embodiment of the vacuum shield assembly according to the present invention attached to nebulizer mask.
Figure 2:
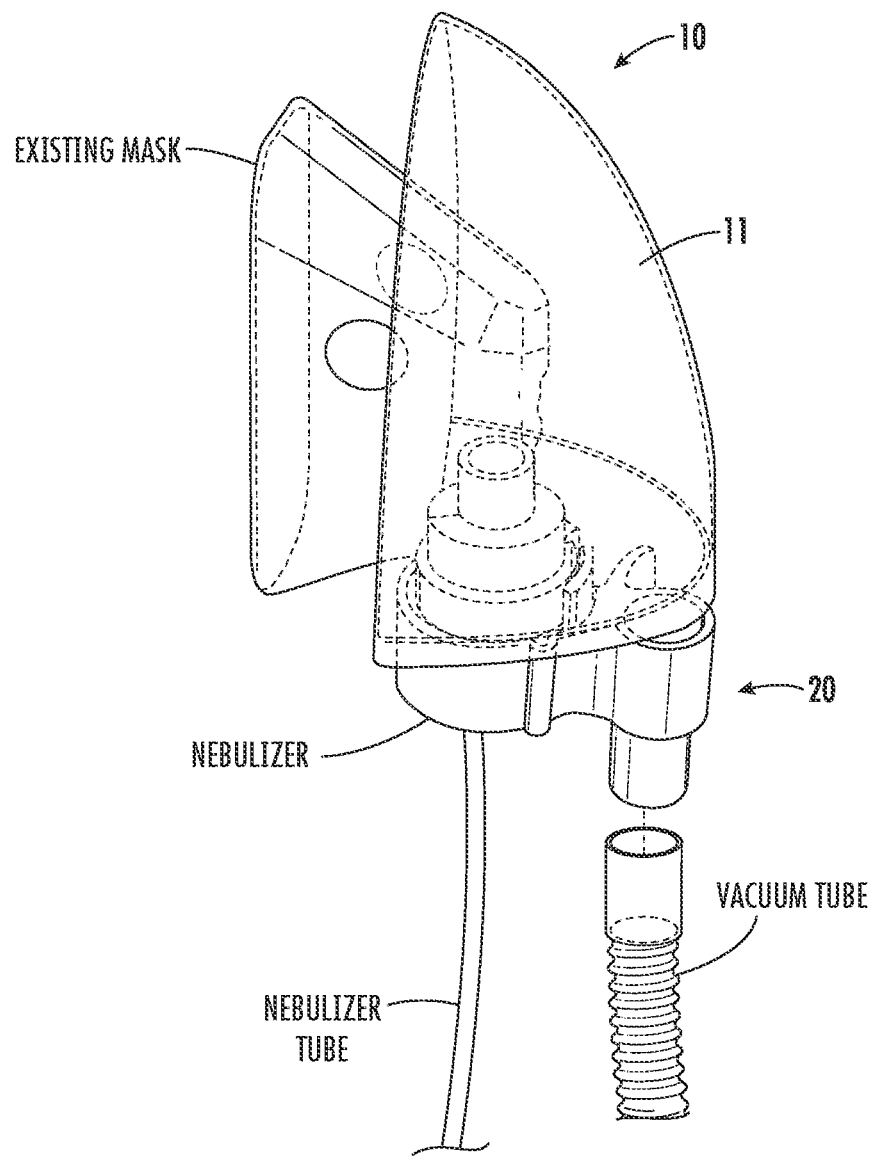
FIG. 2 is a perspective view of another embodiment of the vacuum shield assembly according to the present invention for use with a nebulizer mask.
Figure 3:
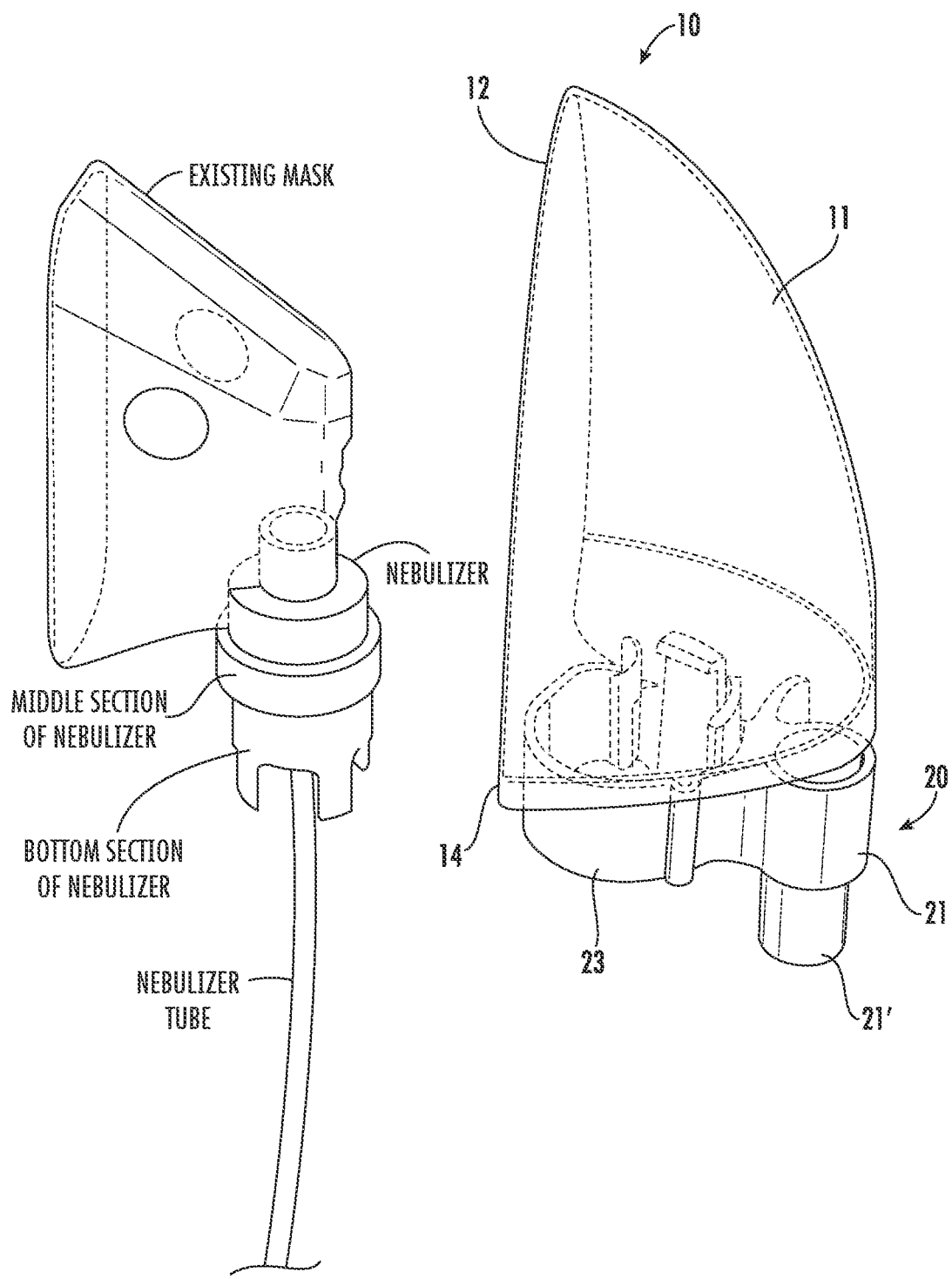
FIG. 3 is a perspective view of yet another embodiment of the vacuum shield assembly according to the present invention for use with a nebulizer mask.
Figure 4:
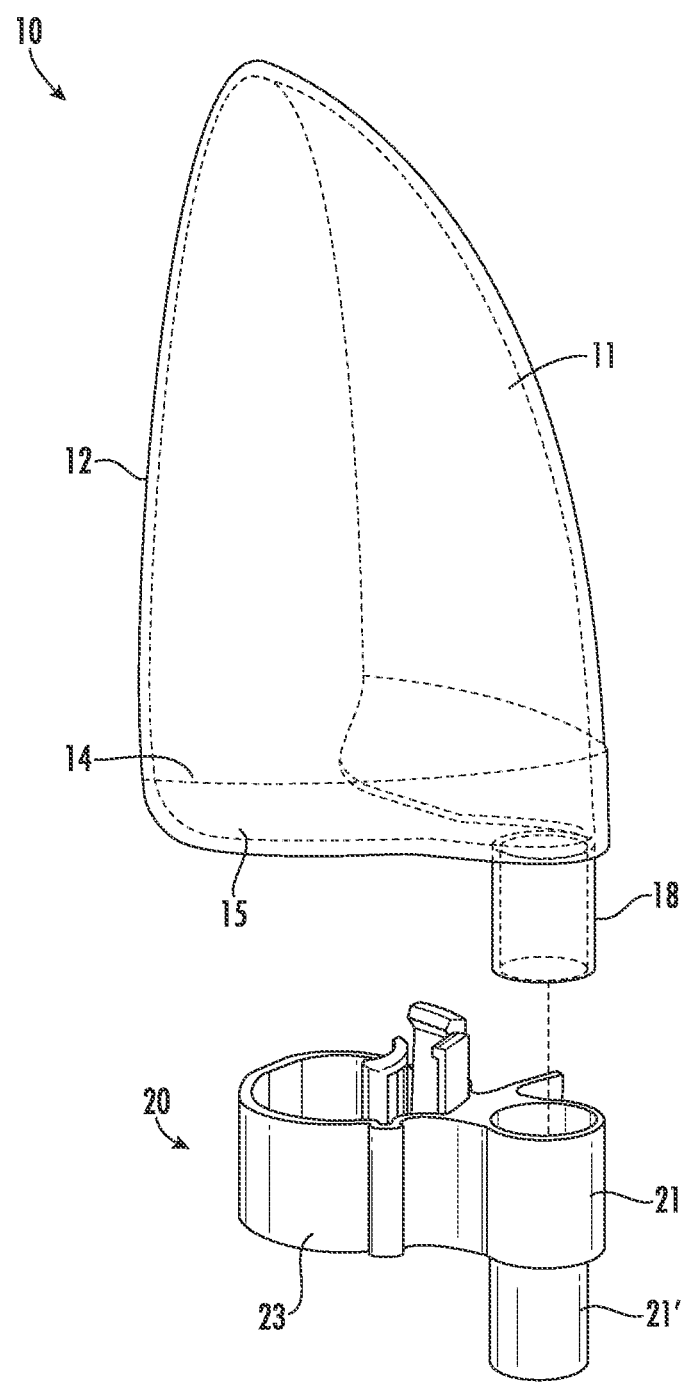
FIG. 4 is a perspective and partially exploded view of a further embodiment of the vacuum shield assembly according to the present invention.
Figure 6:
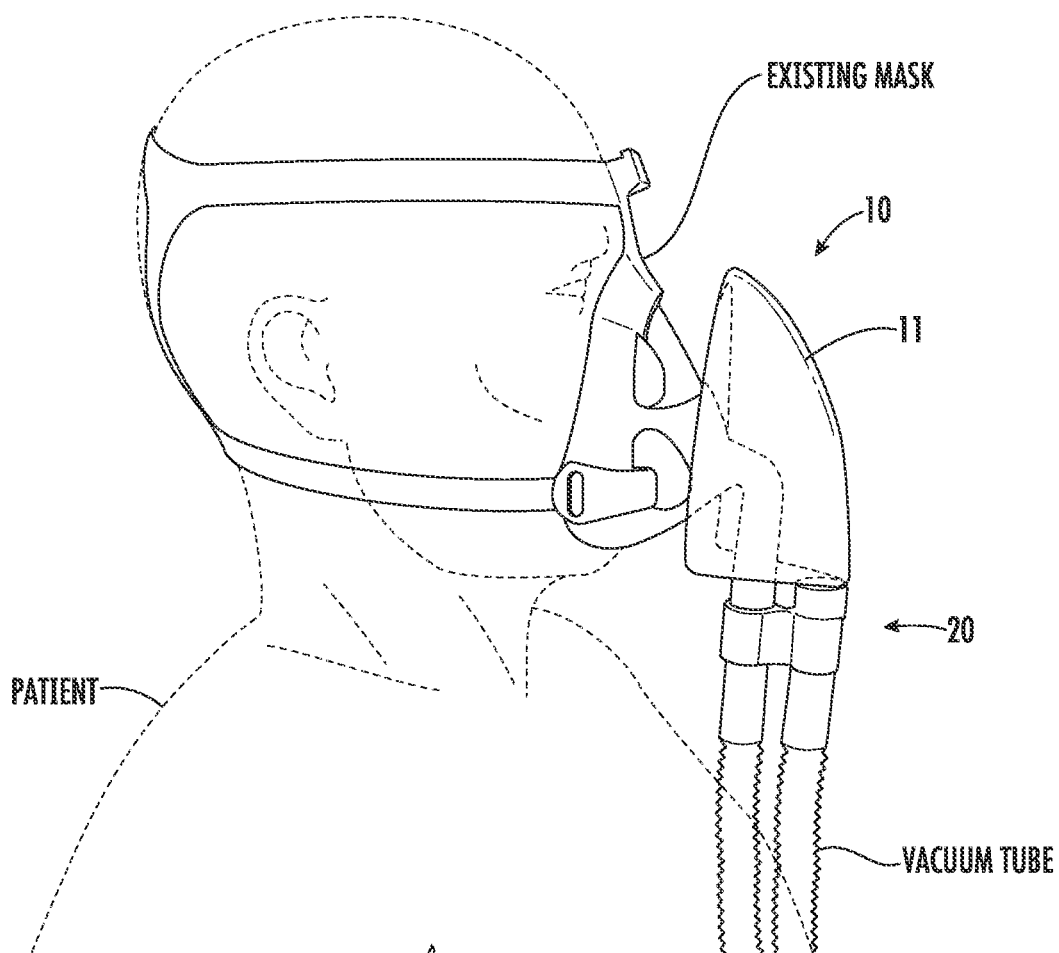
FIG. 6 is a perspective view of one embodiment of the vacuum shield assembly according to the present invention attached to a BIPAP or CPAP mask.
Figure 7:
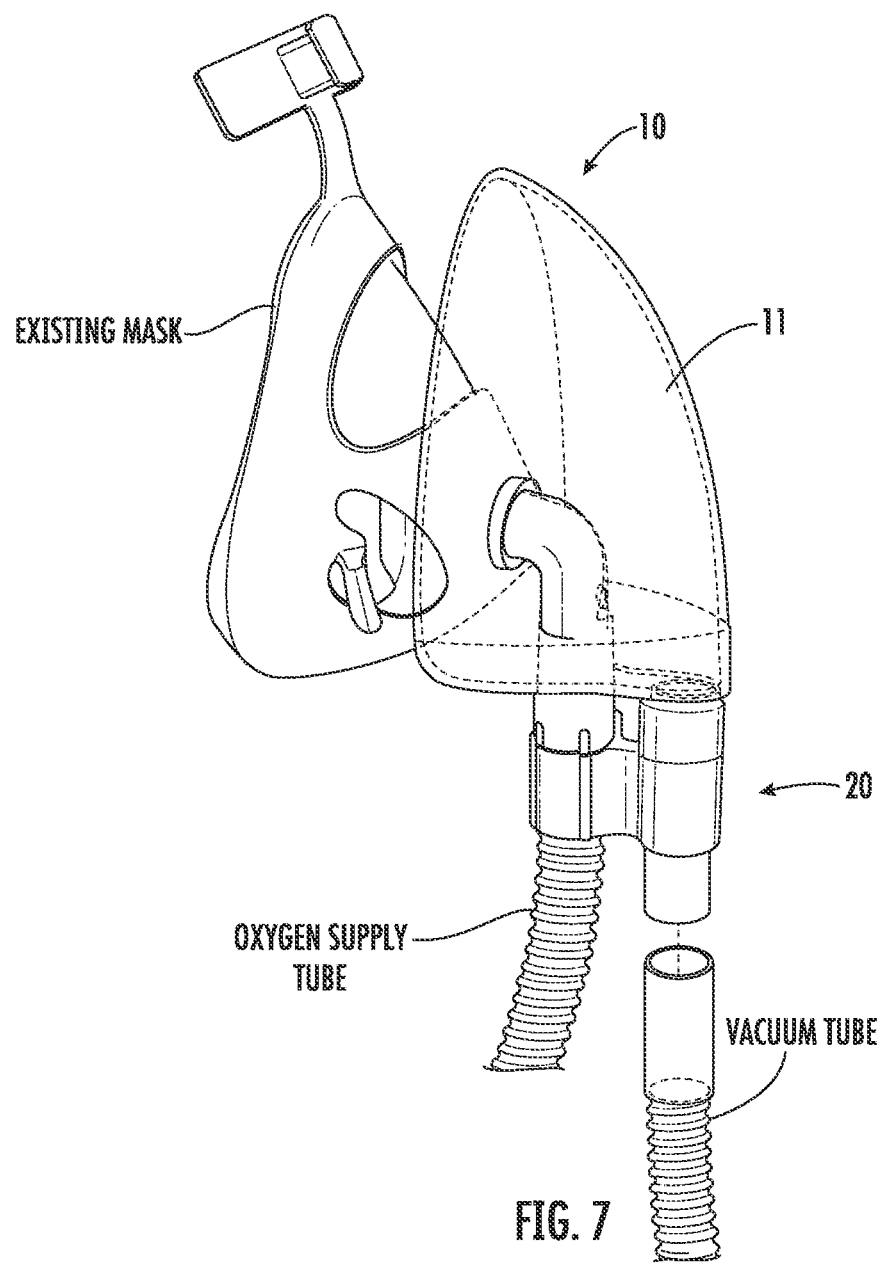
FIG. 7 is a perspective view of another embodiment of the vacuum shield assembly according to the present invention for use with a BIPAP or CPAP mask.
Figure 8:
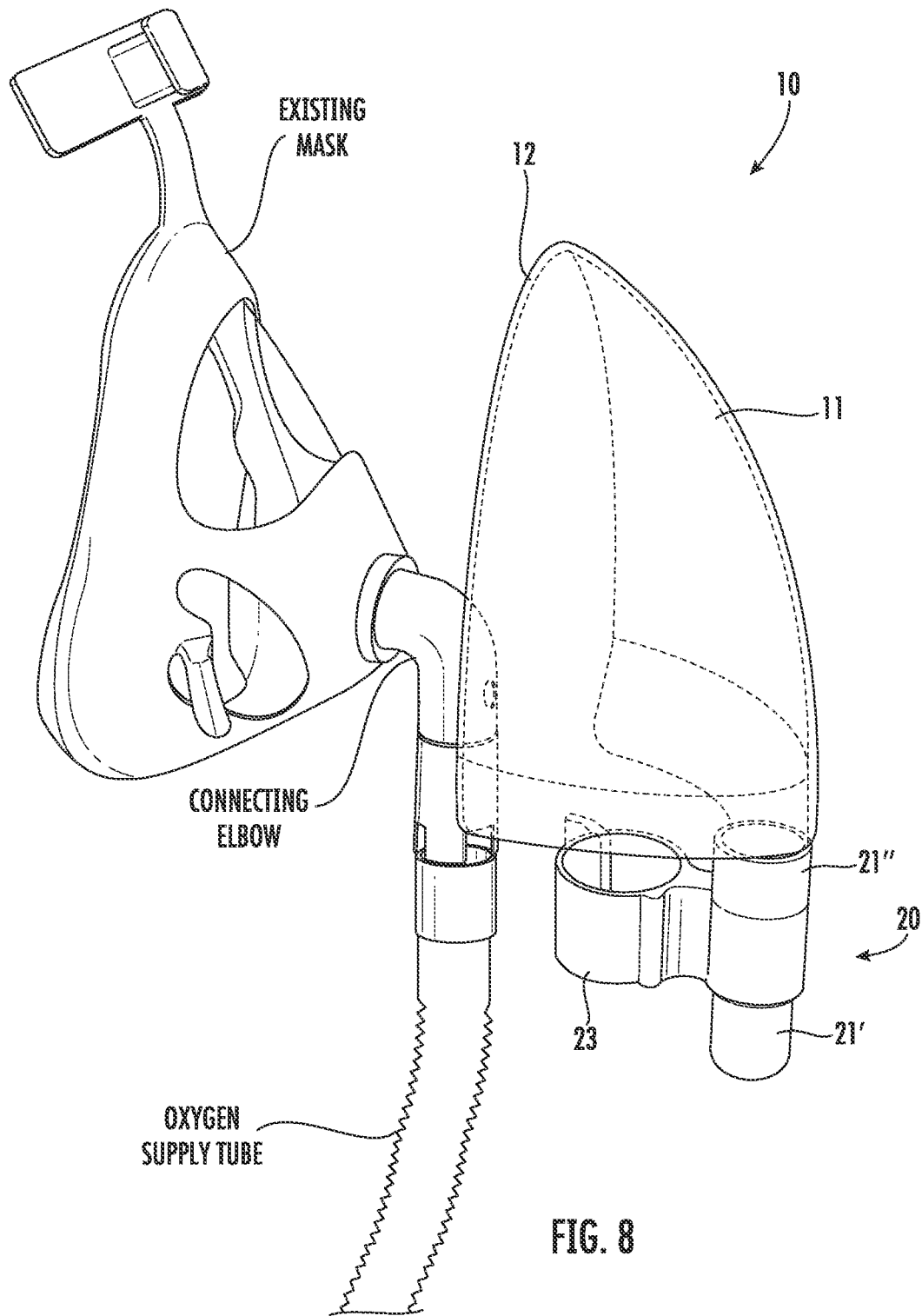
FIG. 8 is a perspective view of yet another embodiment of the vacuum shield assembly according to the present invention for use with a BIPAP or CPAP mask.
Figure 9:
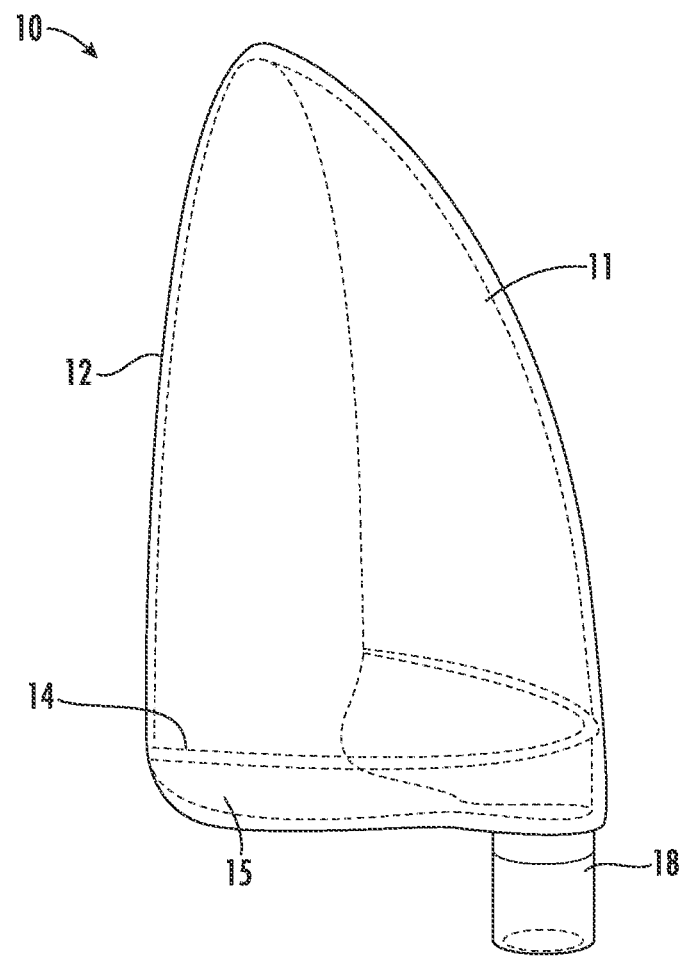
FIG. 9 is a perspective and partially exploded view of an even further embodiment of the vacuum shield assembly according to the present invention.
Figure 9:
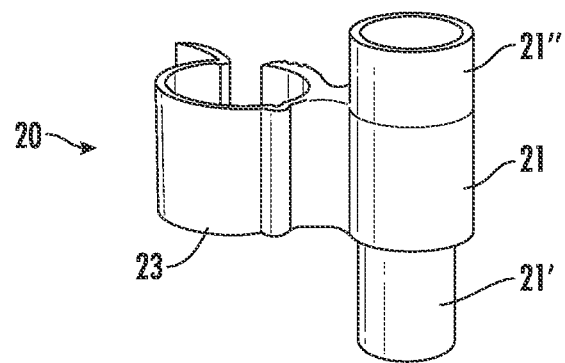
Figure 10:
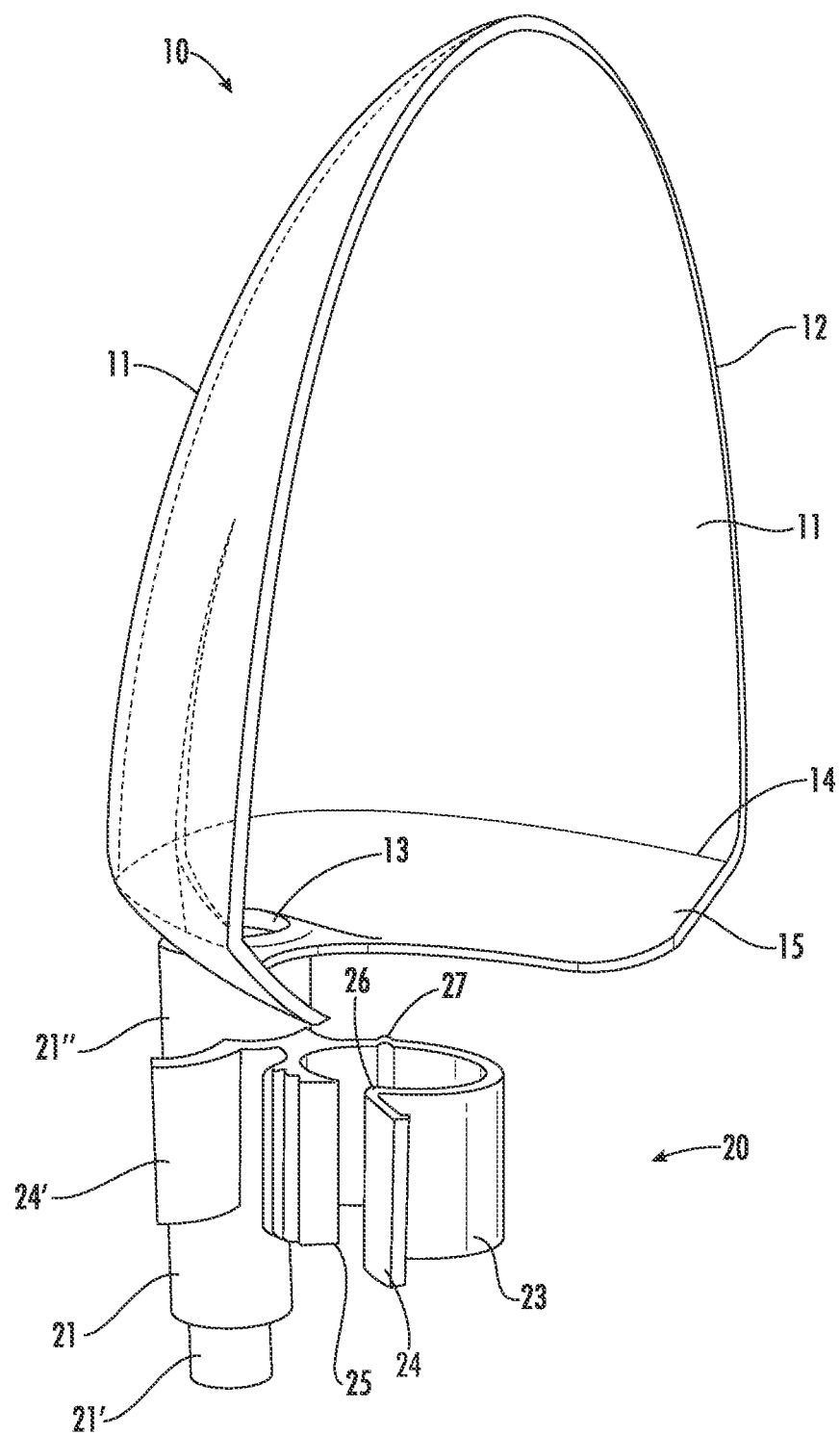
FIG. 10 is a perspective view of yet a further embodiment of the vacuum shield assembly according to the present invention.

With initial reference to FIGS. 1-4, 6-10 and 12, the present invention is directed to a vacuum shield assembly 10. The vacuum shield assembly 10 according to the present invention is intended to be disposed on the head and/or face of a patient that is already wearing a medical mask, and is intended to at least partially extract exhaled air from the patient. For example, and as is perhaps best shown in FIGS. 1 and 6, the vacuum shield assembly 10 may be attached to a mask already disposed on the head and/or face of a patient. The vacuum shield assembly 10 may be connected to a vacuum tube such that it may at least partially extract exhaled air from the patient, including, for example, between the already disposed medical mask and the inside of a shield body 11 of the vacuum shield assembly 10. The vacuum shield assembly 10 may serve as a primary suction or vacuum mechanism, or alternatively, as secondary suction or vacuum mechanism. As an example, and as is shown in FIGS. 6-8, the vacuum shield assembly 10 may be attached to a BIPAP or CPAP mask already disposed on the head and/or face of a patient. As a further example, and as is shown in FIGS. 1-3, the vacuum shield assembly 10 may be attached to a nebulizing mask already disposed on the head and/or face of a patient.

As shown at least in the illustrative embodiments of FIGS. 1-4, 6-10 and 12, the vacuum shield assembly 10 comprises a shield body 11. The vacuum shield assembly 10 also generally comprises a retaining assembly 20. The retaining assembly 20 is generally connected to the shield body 11 as well as to a vacuum tube. As used herein, the term "vacuum tube" refers to a conduit, hose, or other related structure that may convey air from a patient and/or mask to another location, and which may be connected to a negative pressure vacuum. As shown at least in FIGS. 2 and 7, the retaining assembly 20 may be used to interconnect the shield body 11 to a vacuum tube. The structure of the retaining assembly 20 should define a fluid communication between an inside of the shield body 11 and the vacuum tube. As such, the shield body 11 may create a negative pressure on an interior thereof to remove the air between the medical mask, the face and/or head of the patient, and the interior or inside of the shield body 11. It is contemplated that a patient that is wearing a BIPAP or CPAP mask, or a nebulizing mask, be able to exhale through the mask, and that at least a portion of this exhaled air may be captured by the negative pressure generated by the shield body 11 and the vacuum tube.

Figure 12:
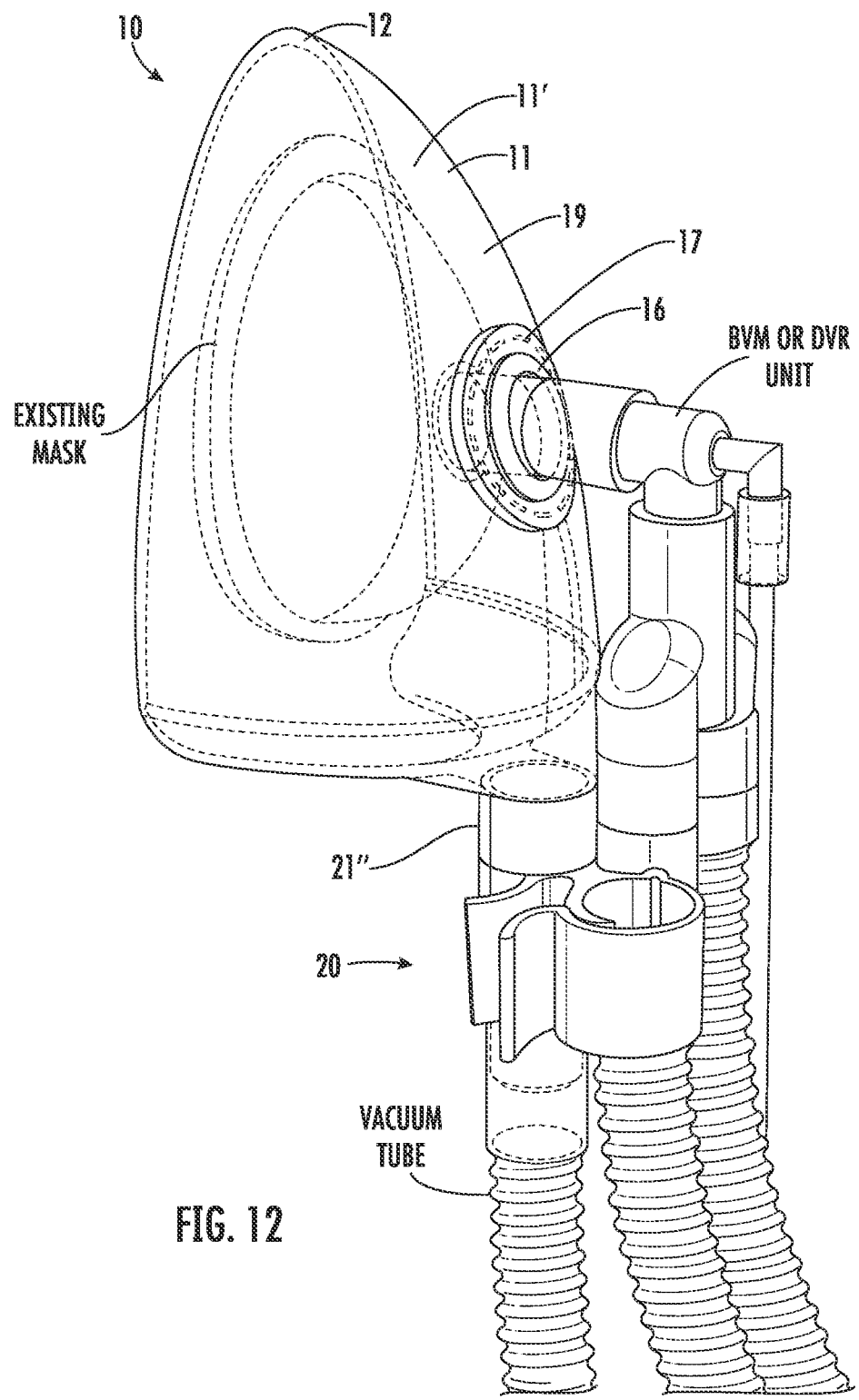
FIG. 12 is a perspective view of one embodiment of a shield body of the vacuum shield assembly according to the present invention.

As is shown in FIGS. 1-2 and 6-7 the retaining assembly 20 may also be used to connect the shield body 11 and/or vacuum tube to an oxygen supply tube and/or a nebulizing unit or component thereof. Shield bodies of different sizes may be attached to a retaining assembly 20, for example, by inserting a connecting portion 18 into an upper section 21" of the retaining component 21, or to the retaining component 21 directly, which will be explained later. As such, it may be possible to switch between shield bodies of different sizes according to a specific need, e.g., air suction, nebulization, etc., and/or geometrical constraints, e.g., the size of the head of the patient. With reference to FIG. 12, in an alternative embodiment, a shield body 12 may be provided with a second opening 16 configured with or without a grommet seal 17. The second opening 16 may be configured for attachment of BVM or DV. The second opening 16 may be disposed on the shield body 12 substantially around a middle section thereof and/or above first opening 13. The second opening 16 also be used for accessing various components of the already disposed mark. For example, vacuum attachment 17 may comprise various components, including seals, elastomeric materials, plastics, or other related structures, that may enable a fluid communication with the interior of the shield body 11 and an external component, including, without limitation, a secondary vacuum tube or BVM or DVR. As may be appreciated from the illustrative embodiment as shown in FIG. 12, exhaled air may exit through the opening 13 of the shield body 12, but in addition to, or in lieu of this, exhaled air may also exit through a vacuum tube operatively connected to the second opening 16.

As is perhaps best shown in FIGS. 5-6, and as mentioned below, the inventive vacuum shield assembly 10 comprises a retaining assembly 20. As shown in FIGS. 1 and 6, the retaining assembly 20 may be oriented towards the face of a patient, such that it may be used to attach the shield body 11 to an existing vacuum tube or other related component. Various connecting mechanism of the retaining assembly 20 may be implemented to connect it to the shield body 11, vacuum tube, oxygen supply tube or nebulizing unit. Said differently, the retaining assembly 20 may be used to interconnect the shield body 11 to the vacuum tube and the oxygen supply tube, an existing nebulizing unit and/or mask, or an existing BIPAP or CPAP mask. As an example, the retaining assembly 20 may comprise clamps or connecting arms. Other mechanisms of the retaining assembly 20 are also within the scope of the present invention and may comprise adhesives, connecting bands, snap-on mechanisms, magnets, or another related connecting mechanisms.

Figure 5:
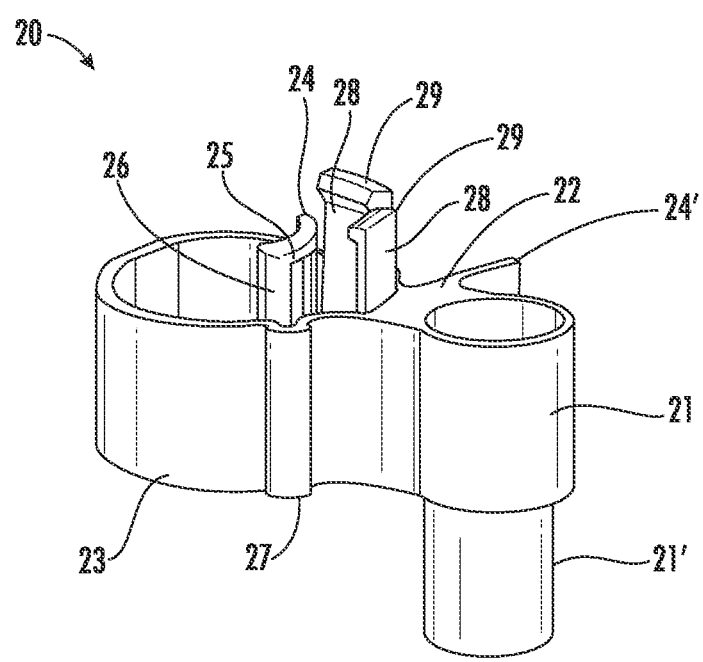
FIG. 5 is a perspective view of one embodiment of a retaining assembly of the vacuum shield assembly according to the present invention.
Figure 11:
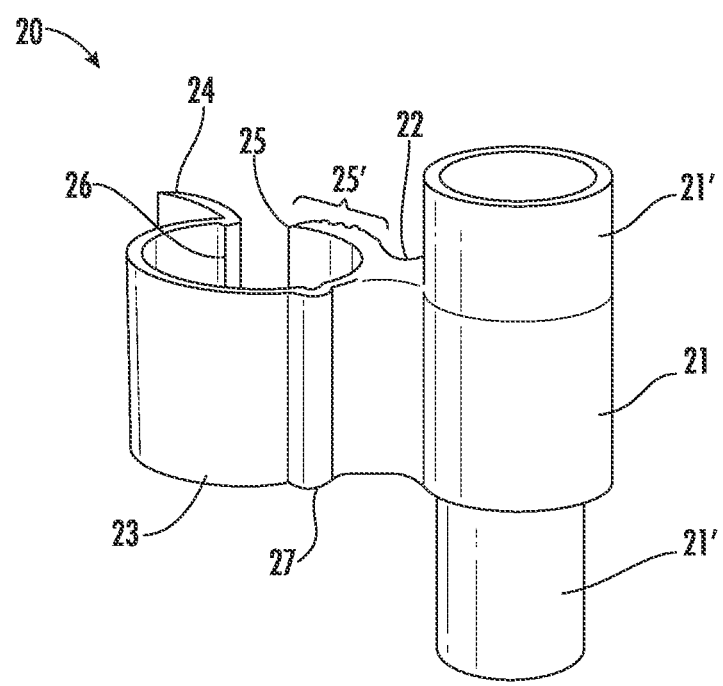
FIG. 11 is a perspective view of another embodiment of a retaining assembly of the vacuum shield assembly according to the present invention.

As seen in the illustrative embodiments of FIGS. 5 and 11, the retaining assembly 20 may comprise a retaining frame 23 connected to a retaining component 21. As mentioned above, a connecting portion 18 of the vacuum shield assembly 10 may be configured and dimensioned to correspond to the size of a retaining component 21 of the retaining assembly 20. As may be appreciated from FIG. 11, sometimes it may be beneficial to provide for a height adjustment for the point of connection between the connecting portion 18 of the shield body 11 and the retaining assembly 20. In such embodiments, the retaining component 21 may be provided with an upper section 21" which may at least partially raise the position of the shield body 11 relative to the point of attachment of the retaining assembly 20 to the oxygen supply tube or other related component of the existing mask.

Additional features of the present invention comprise providing a shield body 11 that may be configured and dimensioned to correspond to the geometry and/or size of the head and/or face of patient and/or the existing mask and its components. It is within the scope of the present invention that when the shield body 11 is disposed against the existing mask that a substantial portion of the edge 12 at least partially surround the existing mask. That is, the shield body 11, including the edge 12 of the perimeter, should define a profile or area that is at least equal to or even greater than the profile or area of the existing mask. As such, exhaled air from the patient will be retained on an inside of the shield body 11, including above a lower segment 15. As an example, as is shown at least in FIGS. 4 and 9-10, the edge 12 may comprise a semi-ovoidal configuration. As is perhaps best shown in FIGS. 4 and 9, the edge 12 may also define a substantially flat side profile of the shield body 11. However, the shield body 11 may comprise other shapes to correspond to the shape of the existing mask. The lower segment 15 may be configured and dimensioned to accommodate the size and/or geometry of an oxygen supply tube of a BIPAP or CPAP mask, or the size and/or geometry of a nebulizer unit and/or components thereof.

The illustrative embodiment of FIGS. 6-9 and 11 show a retaining assembly 20 comprising a retaining component 21 and an upper section 21" thereof which provides for a vertical offset. The length of the upper section 21" may be configured and dimension according to preferences, type of existing mask, intended application, amount of height adjustment needed for the shield body 11, etc. These illustrative embodiments, both of the retaining component 21 and the upper section 21" comprise a substantially cylindrical configuration with approximately the same diameter. Conversely, as is in the illustrative embodiments of FIGS. 1-5, the retaining assembly 20 may be provided with a retaining component 21 without an upper section 21". It is within the scope of the present invention that the connecting portion 18 of the shield body 11 be attachable to the retaining component 21 and/or upper section 21" thereof. For example, the connecting component 18 may comprise a substantially cylindrical configuration, which may be configured and dimensioned to correspond to the size of an inside of a cylindrical retaining component 21 and/or upper section 21". Further to this example, and as is perhaps best shown in FIGS. 4 and 9, the outer diameter of the connecting component 18 may be at least partially smaller than the inner diameter of the retaining component 21 and/or upper section 21", such that the connecting component 18 may be inserted into the retaining component 21 and/or upper section 21". In at least one embodiment the retaining component 21 and upper section 21" may comprise the same diameter. Additionally, in such embodiments, both diameters of the connecting component 18, retaining component 21 and/or upper section 21" may be configured and dimensioned to enable a frictional resistance between corresponding surfaces such that the shield body 11 may be connected to the retaining assembly 20, and further, so that it may remain in place during periods of operation or use of the inventive vacuum shield assembly 10.

As may be perhaps best shown in the illustrative embodiments of FIGS. 2-5 and 7-11, the retaining component 21 of the retaining assembly 20 comprises a lower section 21'. The inside of the lower section 21' of the retaining component 21 should be disposed in fluid communication with the inside of the retaining component 21, the inside of the connecting portion 18 of the shield body 11, the inside of the upper section 21" of the retaining component, and/or the inside of the vacuum tube. Additionally, the lower section 21' of the retaining component 21 may be configured and dimensioned for attachment of the vacuum tube. By way of example only, the lower section 21' of the retaining component 21 may be provided with an outer diameter that is at least partially smaller to an inner diameter of the vacuum tube. As such, the vacuum tube may be attached to the outside of the lower section 21' of the retaining component 21, and may be disposed in fluid communication with an inside of the lower section 21' of the retaining component 21, the inside of the retaining component 21, an inside of the upper section 21" of the retaining component 21, and/or an inside of the connecting portion 18. This should enable a fluid communication between the vacuum tube and the shield body 11, including on an interior or inside thereof, which is perhaps best shown in FIG. 10. As such, activation of the vacuum tube will result in a negative pressure around the inside of the shield body 11. Such a negative pressure will result in at least a partial removal of the air on the inside of the shield body 11 and/or the surrounding area.

With reference to at least FIGS. 5 and 11, and as mentioned above, the retaining assembly 20 may be provided with a retaining frame 23. The retaining frame 23 may be connected to the retaining component 21, for example, via a transition structure 22. The retaining frame 23 is intended to attach the retaining assembly 20, and consequently the shield body 11 and vacuum tube, to a component of the existing mask. For example, such a component of the existing mask may include an oxygen supply tube of a BIPAP of CPAP mask. Also as an example, such a component of the existing mask may also include a nebulizing unit or a portion or component thereof. The retaining frame 23 should comprise an inner area, which may be selectively adjusted to securely retain the oxygen supply tube or nebulizing unit or component thereof. For example, the retaining frame 23 may comprise a substantially cylindrical configuration and/or two segments which may be connected to one another. A first closing structure 25 and a second closing structure 26 may be provided and may be cooperatively configured to form a closing mechanism or engagement that retains the oxygen supply tube or nebulizing unit. Also as an example, the first closing structure 25 and/or second closing structures 26 may be provided with a closing mechanism or related components that may enable such closing mechanism or engagement.

In the illustrative embodiments of FIGS. 1-11, a first closing structure 25 may be provided with a snap component whereas a second closing structure 26 may be provided with serrations 25'. The snap component and the serrations 25' may be cooperatively configured with one another to form a mating engagement, and allow a user or medical practitioner to selectively increase or decrease the inner area of the retaining frame 23. For example, the snap may be selectively disposed in any one of a plurality of serrations 25' along the length of one of the segments of the retaining frame 23. As used herein, a "snap" mechanism generally refers to a single-snap mechanism, or a multi-snap mechanism, i.e., an adjustable mechanism that may be selectively disposed into various size settings. As such, one single retaining assembly 20 may be used in connection with various oxygen supply tubs of different sizes and/or nebulizer units of different sizes. To further assist the user or medical practitioner in adjusting the inner area or opening of the retaining frame 23, one or more flaps 24 and/or 24' may be provided. The flaps 24 and/or 24' may be disposed or otherwise formed on the segments of the retaining frame 23, including around the first closing structure 25 and/or second closing structure 25. The flaps 24 and/or 24' may extend along the height of the retaining frame 23 and/or may comprise a size that corresponds to the size of the thumbs and/or fingers of a user or medical practitioner. Thus, selective movement of the flaps 24 and/or 24' will result in a corresponding movement of at least one of the segments of the retaining frame 23, and consequently movement of a corresponding closing structure 25 and/or 26. Although a retaining assembly 20 may be provided comprising two flaps 24 and 24', it is also possible to provide a retaining assembly 20 comprising only one flap 24 or one without any flaps.

As is perhaps best show in in FIG. 5, the retaining frame 23 may be provided with at least one retaining segment 28 configured to at least partially retain the nebulizing unit. For example, as shown in the illustrative embodiment of FIG. 3, two retaining segments 28 may be used to at least partially retain a middle section of a nebulizing unit. Further, each retaining segment(s) 28 may comprise latch 29 disposed around an upper end thereof. The latch(es) 29 may be configured to hold the top of the middle section of the nebulizing unit in place and at least partially reduce its movement in the vertical direction. As is also shown in the illustrative embodiment of FIG. 3, and also in other embodiments, the retaining frame 23 may be provided with a substantially cylindrical or semi-cylindrical configuration. Such configuration is advantageous to retain or otherwise attach the retaining assembly 20 to substantially cylindrical nebulizers or oxygen supply tubes.

With reference now to at least FIGS. 1-3 and 6-8, features of the present invention comprise providing a vacuum shield assembly 10 with a shield body 11 and a retaining assembly 20 collectively disposable into and out of an operative position and an inoperative position. As used herein, the "inoperative position" refers to a position of non-use of the vacuum shield assembly 10, and may include a storage position, an inactive position, a position where the vacuum shield assembly is not connected to external components, e.g., an oxygen supply tube, vacuum tube, nebulizer unit, face or head of a patient, etc. Conversely, as used herein, the "operative position" refers to an operational or otherwise active positon of the vacuum shield assembly 10. In the operative position, the shield body 11 should be connected to and disposed in fluid communication with the retaining assembly 20. As is shown at least in FIGS. 1-3 and 6-8, in the operative position, an interior or inside of the shield body 11 should be oriented toward the existing mask, which should already be disposed on the face and/or head of the patient. In the operative position, the vacuum tube, and/or connected vacuum source, should exert a negative pressure, which should result on a corresponding exerted negative pressure around the shield body 11 and the surrounding area. It is contemplated that in the operative position, the negative pressure exerted around the inside or interior of the shield body 11, and/or above the lower segment 15, should be sufficient to at least partially extract the exhaled air form the patient. Also, the lower segment 15, along with the interior or inside of the shield body 11, is intended to at least partially retain exhaled air between the face of the patient and/or existing mask, and the shield body 11. As such, movement of the exhaled patient air outside of the area surrounding the shield body 11 may be at least partially reduced, such that, the negative pressure of the vacuum tube, should result on an efficient removal of the exhaled air.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A vacuum shield assembly disposable onto a patient wearing a medical mask and configured to remove exhaled air from the patient, said vacuum shield assembly comprising:
   a shield body comprising a concave configuration,
   a lower segment disposed around a lower perimeter of said shield body, said lower segment comprising an opening,
   said concave configuration of said shield body configured and dimensioned to at least partially surround the medical mask,
   said shield body disposed in proximity, but in a spaced apart relation to the medical mask and the patient,
   a retaining assembly structured to retain a vacuum tube and an oxygen supply tube or a nebulizer unit of the medical mask,
   said retaining assembly adjacently disposed to said lower segment,
   said retaining assembly comprising:
      a retaining component configured and dimensioned to retain a connecting portion of said shield body,
      a lower section of said retaining component configured and dimensioned for attachment of the vacuum tube, and
      a retaining frame connected to said retaining component and configured to retain the oxygen supply tube or the nebulizer unit of the medical mask,
      at least one retaining segment disposed on said retaining frame; said at least one retaining segment configured to at least partially retain the nebulizer unit,
      said at least one retaining segment comprising a latch disposed on an upper end thereof; said latch structured to at least partially reduce movement of the nebulizer unit in a vertical direction,
      said lower segment configured for attachment to the vacuum tube below said lower perimeter of said shield body and configured to exert a negative pressure on an inside of said shield body, and
   said shield body and said retaining assembly collectively disposable into and out of an operative position and an inoperative position.

2. The vacuum shield assembly as recited in claim 1 wherein said shield body is configured to be adjacently disposed to and facing the medical mask when in the operative position.

3. The vacuum shield assembly as recited in claim 2 wherein said concave configuration is structured to define a space around the oxygen supply tube or the nebulizer unit of the medical mask.

4. The vacuum shield assembly as recited in claim 1 wherein said operative position further comprises the vacuum tube configured to exert a negative pressure on an inside of said shield body at least partially removing exhaled air from the patient between said shield body and the medical mask.

5. The vacuum shield assembly as recited in claim 1 wherein said lower segment comprises a substantially curved configuration.

6. The vacuum shield assembly as recited in claim 1 wherein said shield body further comprises an edge defining a flat side profile of said shield body.

7. The vacuum shield assembly as recited in claim 6 wherein said edge comprises a semi-ovoidal configuration.

8. The vacuum shield assembly as recited in claim 1 wherein said shield body further comprises a connecting portion disposed in fluid communication with said opening of said shield body.

9. The vacuum shield assembly as recited in claim 1 wherein said retaining frame comprises a semi-cylindrical configuration.

10. The vacuum shield assembly as recited in claim 1 wherein said retaining assembly comprises a first closing mechanism and a second closing mechanism.

11. The vacuum shield assembly as recited in claim 10 wherein said retaining frame comprises a semi-cylindrical configuration; said first closing mechanism comprising a plurality of serrations; said second closing mechanism comprising a snap mechanism operatively configured and dimensioned with said plurality of serrations to adjust a sleeve size of said retaining frame.

12. The vacuum shield assembly as recited in claim 10 wherein said first closing mechanism comprises a first flap and said second closing mechanism comprises a second flap; said first flap and said second flap cooperatively configured to adjust said inner area of said retaining frame.

13. The vacuum shield assembly as recited in claim 1 wherein said retaining component comprises an upper section configured and dimensioned to retain said connecting portion of said shield body.

14. A vacuum shield assembly disposable onto a patient wearing a nebulizer mask and configured to remove exhaled air from the patient, said vacuum shield assembly comprising:
   a shield body comprising a concave configuration, a lower segment disposed on a lower perimeter of said shield body, said lower segment comprising an opening, said shield body configured and dimensioned to at least partially surround the nebulizer mask, said shield body disposed in proximity to, but in a spaced apart relation to the nebulizer mask and the patient, a retaining assembly structured to retain a vacuum tube and a nebulizer unit of the nebulizer mask; said retaining assembly comprising:

a retaining component comprising a cylindrical shape and configured and dimensioned to retain a connecting portion of said shield body, said retaining component comprising a diameter that is less than a diameter of the connecting portion of said shield body, an interior of said retaining component disposed fluid communication with said interior of said shield body and an interior of the vacuum tube, a lower section of said retaining component comprising a cylindrical shape and configured and dimensioned for attachment of a vacuum tube, said lower section of said retaining component comprising a diameter that is smaller than a diameter of the vacuum tube;

a retaining frame comprising a semi-cylindrical configuration and connected to said retaining component; said retaining frame configured to retain the nebulizer unit of the nebulizer mask, said retaining frame comprising at least one retaining segment extending above said retaining frame, said retaining segment comprising a latch around a top portion thereof, said latch configured and dimensioned to retain a top surface of a middle section of a nebulizer unit and to reduce movement of the nebulizer unit in the vertical direction;

said lower segment configured for attachment to the vacuum tube below said lower perimeter of said shield body and to exert a negative pressure on an inside of said shield body, and said shield body and said retaining assembly collectively disposable into and out of an operative position and an inoperative position;

said operative position comprising the vacuum tube exerting a negative pressure on an inside of said shield body least partially removing exhaled air from the patient between said shield body and the nebulizer mask.

\* \* \* \* \*